United States Patent [19]

Nielsen

[11] Plant 4,340

[45] Dec. 5, 1978

[54] EUONYMUS PLANT

[75] Inventor: Peter R. Nielsen, Oakville, Canada

[73] Assignee: Dugan Nurseries Incorporated, Perry, Ohio

[21] Appl. No.: 867,829

[22] Filed: Jan. 9, 1978

[51] Int. Cl.[2] ..... A01H 5/00

[52] U.S. Cl. ..... Plt./63

[58] Field of Search ..... Plt./63

*Primary Examiner*—Robert E. Bagwill

*Attorney, Agent, or Firm*—Beall & Jeffery

[57] ABSTRACT

The new cultivar Sunspot is especially characterized by its broadleaf evergreen foliage which has pronounced yellow centers with dark green margins of irregular depth, with the leaves inside the plant being of the same variegated color as the stem tips, thereby giving the plant as a whole a distinctive and striking yellow spotted appearance.

2 Drawing Figures

The present invention comprises a new and distinct cultivar of *Euonymus fortunei*, hereinafter referred to by the cultivar name of Sunspot.

Sunspot is a sport of the unpatented Euonymus plant known by the cultivar name Emerald Cushion, and the sport was discovered by me in Oakville, Ontario, Canada, in the form of a branch of the patent cultivar in which the foliage was variegated. The sport was observed due to the unique showing of a golden spot in the center of the green leaf, and by the stems of the plant being yellow in color. Continued observation of the sport, as well as the subsequent asexually reproduced plants thereof, convinced me that the sport is both new and distinct from the parent cultivar, as well as from all other cultivars of Euonymus plants of which I am aware.

The following unique combination of characteristics have been repeatedly observed and serve to distinguish Sunspot as a new and distinct cultivar:

1. A distinctive variegation pattern in which a yellow spot or area is surrounded by the normal green foliage color.
2. Unusually showy yellow stem color;
3. Improved foliage and stem color stability into fall and winter seasons, when compared to the parent cultivar and when compared especially to other variegated Euonymous cultivars presently available.
4. Improved vigor and lengthened growing season compared to the parent cultivar, and especially compared to other variegated Euonymus cultivars, which tend to go dormant earlier.
5. An attractive rounded plant shape, in contrast to the low, broad habit of growth of the parent cultivar.
6. An unequaled visibility of the variegated characteristic even when viewed from a distance, due to the extreme difference between the green and yellow colors which provide the variegation, which gives the entire plant a distinct and attractive spotted appearance.

Asexual reproduction of Sunspot in Oakville, Ontario, Canada by cuttings has established that the foregoing characteristics and distinctions come true to form and are established and transmitted through succeeding propagations.

The accompanying photographic drawings illustrate, in the first photograph, a typical 2 year old specimen plant of the new cultivar, and in the second photograph a close-up of a single branch of the cultivar, showing in more detail the leaf and stem characteristics. The color in the photographs is as nearly true as possible in color renditions of this type.

The following is a detailed description of the new cultivar, with color values being referenced to the Royal Horticulture Society Colour Chart, except where general color terms of ordinary dictionary significance are used. The color values were taken in Ashtabula, Ohio at around 2:00 P.M. on approximately Nov. 20, 1977.

Form: Rounded, dense, compact, moderate growing, not as low or as broad as the parent cultivar Emerald Cushion.

Growth:

*Two year old plants.*—Height, from about 15 to 18 inches. Breadth, from about 15 to 18 inches.

*Mature plants.*—Height, from about 3 to 4 feet. Breadth, from about 3 to 4 feet.

Hardiness: Good winter hardiness as evidenced by the fact that plants grown outdoors have withstood winter temperatures of U.S.D.A. hardiness Zone 5 with little protection, and U.S.D.A. hardiness Zone 4 with some wind protection.

Stems (branchlets): Smooth, dull; color, intense yellow, group 11-A, with occasional green streaking. Occasional aerial roots.

Axillary buds: Elongate, conical.

Foliage:

*Type.*—Broadleaf evergreen, petioled, opposite.

*Shape.*—Ovate to elliptic.

*Petioles.*—Length, 2 to 4 mm.; color, yellow group 11-A.

*Size of leaf.*—Length from 2 to 3 cm., breadth from 1 to 2 cm.

*Leaf texture.*—Heavy compared to parent Emerald Cushion; leathery, smooth, upper surface glossy, lower surface dull. Leaves with more yellow variegation exhibit an attractive curling or waving margin.

*Veining.*—On leaf underside only the midrib is visibly veined; on leaf upper surface veins are difficult to see.

*Leaf margins.*—Crenate, serrate.

*Color.*—Center of leaf, upper side, vivid Yellow, Group 10 between A and B, with areas of stronger concentration toward A. Center of leaf, under side, yellow Group 10 between B and C. Edges of leaf, upper side, deep green group 147-

A. Edges of leaf, under side, green group 147-B. Entire underside of leaf exhibits a faint pink sheen when viewed at a certain angle. On newly expanding leaves all colors tend towards a lighter green, but darken quickly so that new leaves when fully expanded are very close in color to the oldest leaves on a given plant.

I claim:

1. A new and distinct cultivar of *Euonymus fortunei*, known by the cultivar name Sunspot, and characterized particularly as to uniqueness by the combined characteristics of rounded, compact and shapely habit of growth; good winter hardiness, and thick broadleaf evergreen foliage having pronounced yellow centers with dark green margins of irregular depth, with the leaves inside the plant being of the same variegated color as the stem tips, thereby giving the plant as a whole a distinctive and striking yellow spotted appearance.

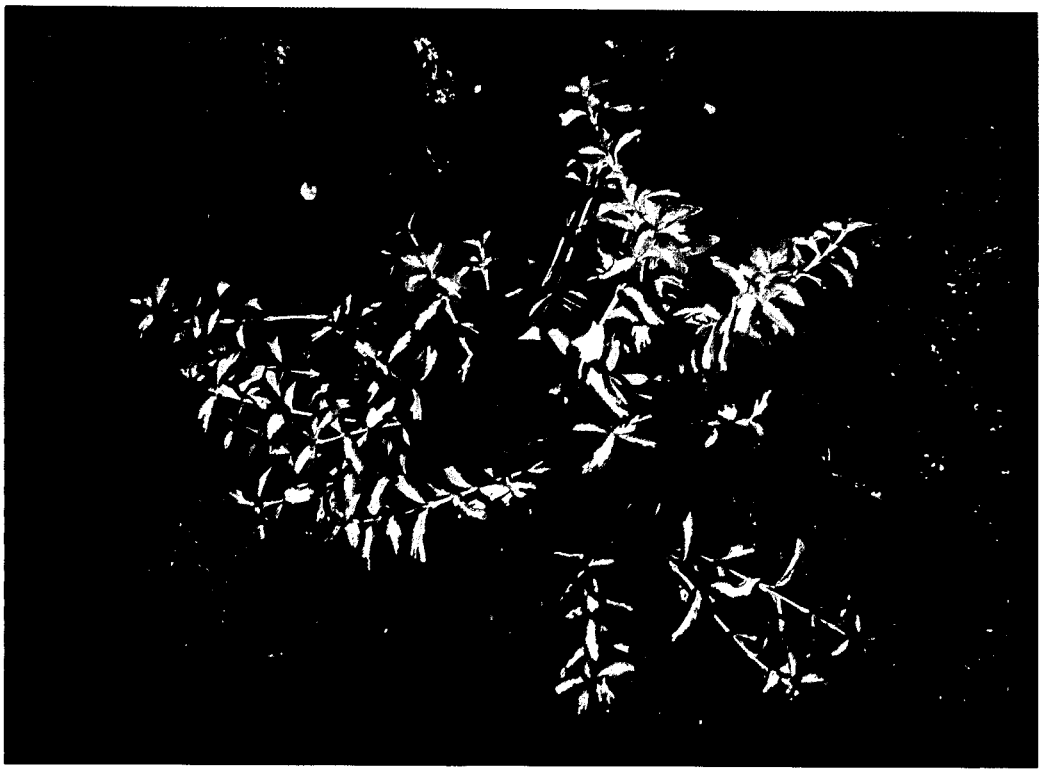

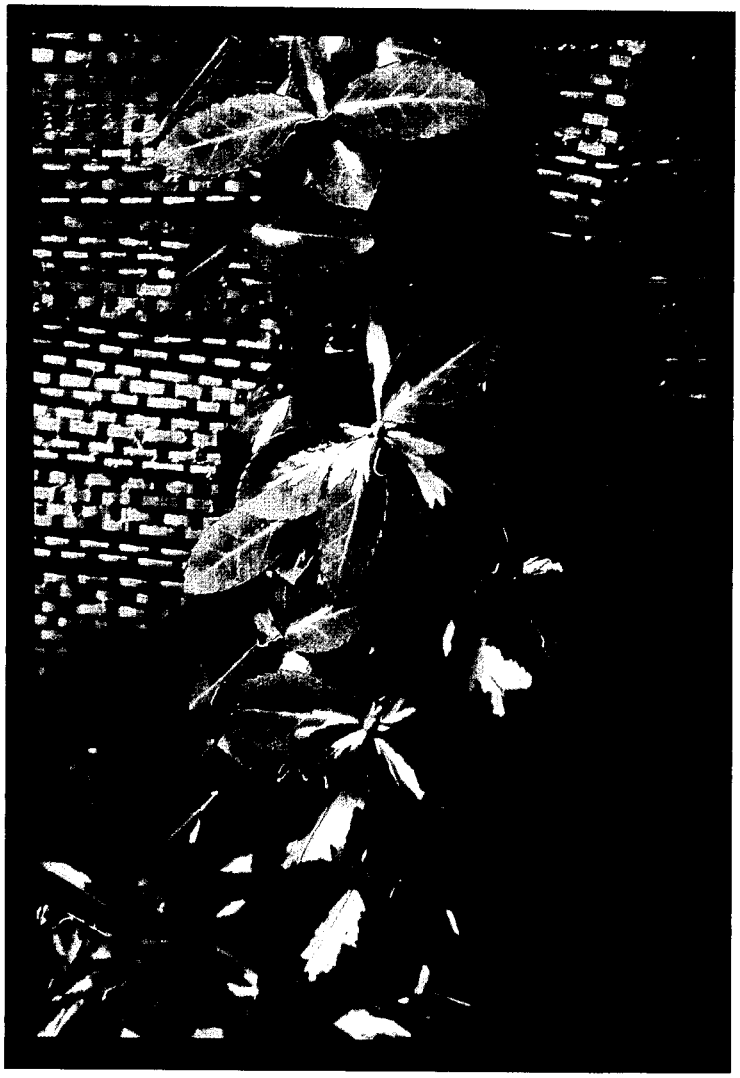

* * * * *